United States Patent [19]

Jones

[11] Patent Number: 5,170,191

[45] Date of Patent: Dec. 8, 1992

[54] TARGET DOMAIN PROFILING OF TARGET OPTICAL SURFACES USING EXCIMER LASER PHOTOABLATION

[75] Inventor: William F. Jones, Pittsford, N.Y.

[73] Assignee: Bausch & Lomb Incorporated, Rochester, N.Y.

[21] Appl. No.: 781,797

[22] Filed: Oct. 23, 1991

Related U.S. Application Data

[63] Continuation of Ser. No. 525,515, May 18, 1990, Pat. No. 5,061,342.

[51] Int. Cl.$^5$ ............................ G02C 3/04; B44C 1/22
[52] U.S. Cl. ............................... 351/160 H; 156/643; 156/654; 156/668
[58] Field of Search ...................... 156/643, 654, 668; 219/121.68, 121.69, 121.73, 121.8; 264/1.4, 22, 25, 2.7; 351/160 R, 160 H, 161, 174, 177

[56] References Cited

U.S. PATENT DOCUMENTS

| | | | |
|---|---|---|---|
| 4,194,814 | 3/1980 | Fischer | 351/160 |
| 4,219,721 | 8/1980 | Kamen | 219/121 |
| 4,307,046 | 12/1981 | Neefe | 264/1.4 |
| 4,563,565 | 1/1986 | Kampfer | 219/121 |
| 4,642,439 | 2/1987 | Miller | 219/121 |
| 4,744,647 | 5/1988 | Meshel | 351/177 |
| 4,838,266 | 6/1989 | Koziol | 128/303.1 |
| 4,909,818 | 3/1990 | Jones | 65/31 |
| 5,053,171 | 10/1991 | Portney et al. | 219/121.67 X |

FOREIGN PATENT DOCUMENTS

| | | |
|---|---|---|
| 16145-88 | 5/1988 | Australia . |
| 0264255 | 4/1988 | European Pat. Off. . |
| 0366356 | 5/1990 | European Pat. Off. . |

Primary Examiner—William A. Powell
Attorney, Agent, or Firm—David M. Krasnow

[57] ABSTRACT

A method for inducing cylinder power into an optical surface which comprises the steps of providing a target optical surface to an apparatus capable of indexing the position of said target to the beam path of a laser capable of photoablating the material of said target, passing said target through the domain of said laser along at least one axis and controlling the product of the intensity of said laser with time in order to control the amount of ablation of said target along at least one axis of said target.

9 Claims, 5 Drawing Sheets

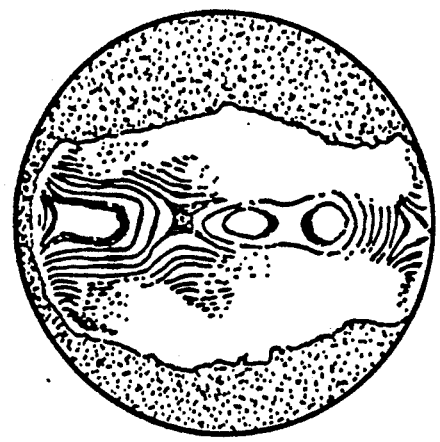
FIG_7
FIG_8
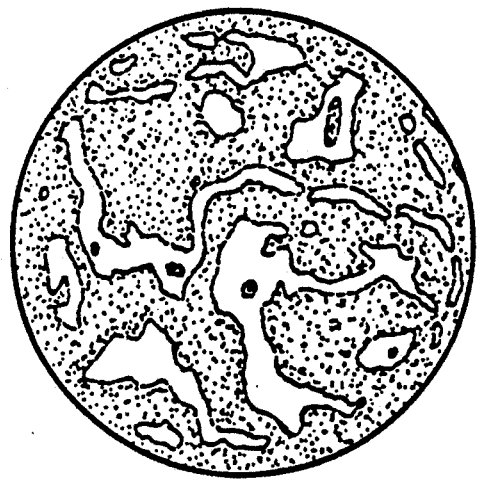

TARGET DOMAIN PROFILING OF TARGET OPTICAL SURFACES USING EXCIMER LASER PHOTOABLATION

This is a continuation of copending application Ser. No. 07/525,515 filed on May 18, 1990, U.S. Pat. No. 5,061,342.

BACKGROUND OF THE INVENTION

A number of methods are known for shaping optical surfaces. Perhaps, the oldest known method is the use of a lathe to reconfigure the surface of an optical article. This method, of course, dates back to the first lenses and the method is used even to the present.

Methods have also been developed for casting or molding optical surfaces. Even these methods, however, depend upon lathing techniques to generate the mold pieces being used to mold the finished optical article. More recently, the idea of using a high energy laser to selectively ablate the surface of an optical article has been put forth.

The present invention allows the use of an excimer laser to selectively alter the surface of an optical article and provides a highly effective and precise means for doing so.

SUMMARY OF THE INVENTION

The present invention involves a method for reconfiguring the surface of an optical article. The present invention is particularly useful in producing toric surfaced optical articles with much more accuracy and precision than have been heretofore available.

BRIEF DESCRIPTION OF THE FIGURES

FIG. 7 shows an interferogram of a commercially available toric contact lens.

FIG. 8 shows the interferogram of a lens whose spherical power has been changed by the present invention.

DETAILED DESCRIPTION OF THE INVENTION

The present invention relates to a new method of modifying optical surfaces to produce changes in their spherical or cylindrical refractive power. This new method employs high energy radiation to ablate material from a contact lens blank in a controlled fashion in order to produce a desired contact lens configuration.

In particular, the method takes advantage of the relatively fixed pulse beam intensity of an excimer laser beam to sweep across the domain of an optical surface. By controlling the rate at which a beam is swept across the target along a given axis, the degree of ablation along that axis at any given point can be controlled.

A beam from an excimer laser is roughly rectangular in cross-section and has a roughly uniform radiation intensity across one axis of symmetry. The beam intensity is also not absolutely uniform, however, its profile can be measured and accounted for in the process. The main aspect of the beam which is substantially fixed is the pulse intensity profile. This characteristic allows, according to invention claimed and described, to control the photoablation of an optical surface.

Figure 1:
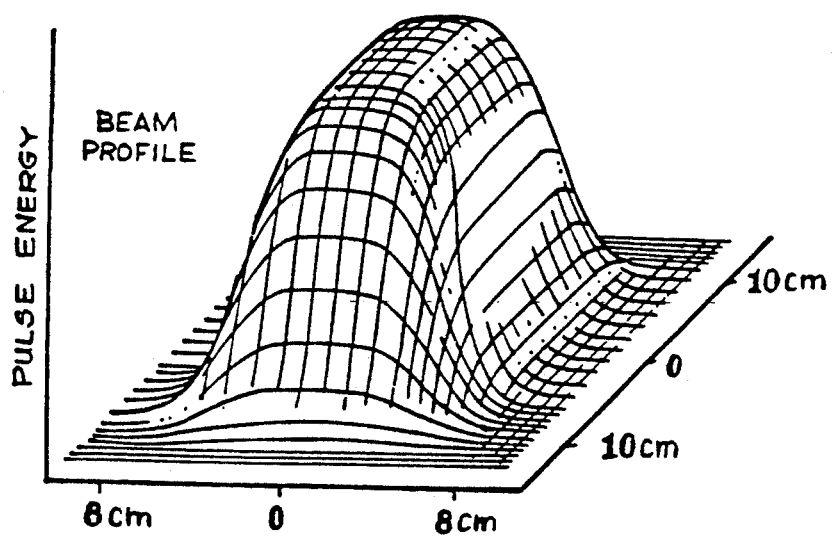
FIG. 1A is the graphical representation of the shape of the cross-section of an excimer laser beam and shows of the energy distribution of the excimer laser in its x and y coordinates respectively.

FIG. 1 shows a typical cross-section of an excimer laser along with the intensity distributions of the laser along its x and y coordinates. As can be appreciated, the intensity across the x axis of the beam is substantially uniform everywhere except at the edges. The invention describes a method for truncating the beam edges and thus provides a beam to the target of uniform intensity.

Controlled ablation of the complete lens surface is accomplished by scanning the beam along its y axis across the optical surface being altered. When this scanning is done at a fixed velocity, the effect is simply to broaden the y axis of the beam profile as experienced by the target optical surface.

It should be noted that excimer lasers operate in short pulses of about 20 nanoseconds and has a total pulse energy very consistent from pulse to pulse. The ablation process contemplated here requires a multitude of pulses in order to accomplish the desired objective. During the ablation process, which typically lasts from 0.1 to 30 seconds, the excimer laser beam domain can be scanned across the target optical surface in a fashion to effect a linear or nonlinear, smooth and continuous ablation profile along one of the target's axes.

Figure 2:
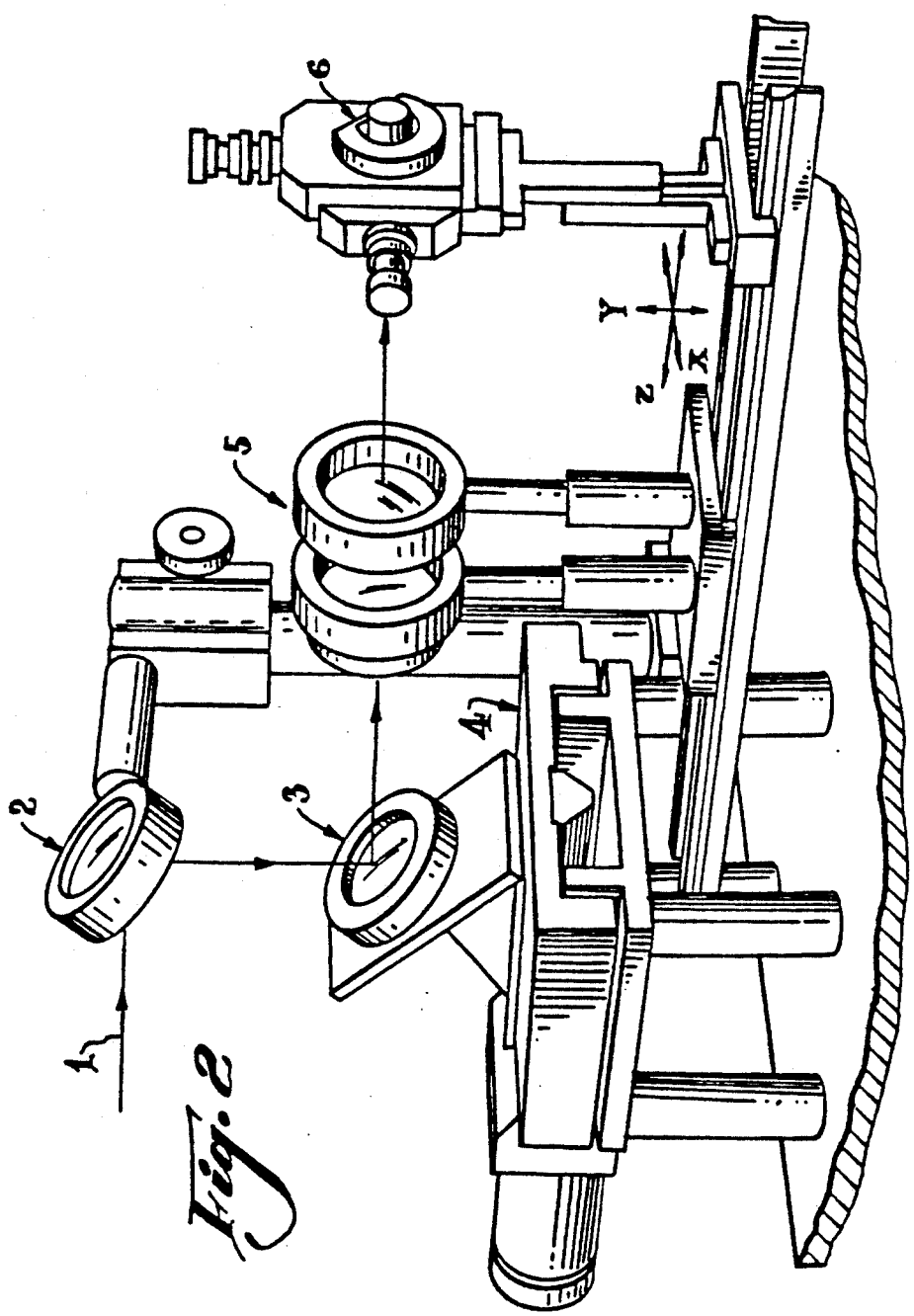
FIG. 2 is an illustration of an apparatus used to practice the present invention where the laser beam is scanned across the surface of the target contact lens blank.

Scanning the excimer laser beam can be accomplished by at least two means. FIG. 2 shows an approach where the beam (1) is reflected 90° by a 45 degree fixed reflecting mirror (2). The beam is then reflected 90 degrees by a scannable mirror (3), which may be a total reflectance mirror or which can be a partial transmittance mirror. In the event that either mirror is a partial transmittance, mirror means for monitoring the beam profile of the excimer laser can be provided. Means for moving the scanning mirror (4) parallel to the initial beam path are provided which allows the mirror to shift the beam from its incident path and scan the beam domain across the target optical surface.

Another method of practicing the invention involves the use of a mirror whose angle of incidence to the beam can be varied in order to sweep the beam domain across the target optical surface. In place of the fixed angle mirror(3) in the apparatus shown in FIG. 2 the mirror would be allowed to pivot in the plane of the axis being swept by the laser through the target. No other means, such as the linear servo-mechanism (4) found in the diagram would be necessary to effect the beam scanning, although a combination of linearly scanning the mirror in conjunction with pivoting the lens could be used.

Assuming the laser intensity and pulse rate of the laser to be substantially consistent, the degree of photoablation will be related to the velocity of the mirror (2) as it moves along axis of z, and the ablation would be uniform across the target optical surface in the event the mirror velocity was constant.

Since photoablation as a function of y is related to the instantaneous velocity of the beam along the y axis (or the velocity of the mirror along the z axis) one can control the degree of photoablation by controlling the velocity profile of the mirror as it sweeps the beam across the target domain.

FIG. 2 also shows the apparatus as having a lens (5) which reduces the beam and thus increases the intensity of the beam as it is incident on the target (6). It should be understood that this element is optional in the practice of the invention, the beam could be used in the present invention without reducing its cross-sectional dimensions.

The mathematical expression of the relation of ablation to the scanning of the pulsed beam is described as:

$$T = K.H.N/V \qquad (1)$$

where
T is the thickness of material removed;
K is a constant;
H is the repetition rate of the laser (pulse rate);
N is the number of scans; and
V is the instantaneous velocity of the beam.

Figure 3:
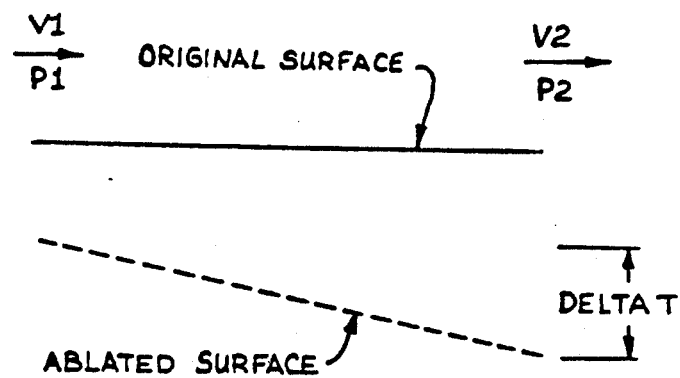
FIG. 3 is a schematic representation of an optical target which defines certain dimensions critical to the relationship of the scanning modality to ablation profile.

In the event that a continuous laser is employed the relationship could be expressed as $$T = K^1 N/V \qquad (2)$$

where K1 is a constant. Both K and K1 are constants for the ablation of a given material in a specific environment. Thus, these constants are dependent upon target material composition, atmospheric conditions ambient to the target, wavelength of the beam, and beam intensity.

Where the scanning rate is non-uniform, ablation along the target axis will be defined as $$\text{delta } T = K.H.N(V2 - V1)/(V1.V2) \qquad (3)$$

where V1 and V2 are the velocities of the beam on the target at points P1 and P2, and delta T is the difference in material removal between the two points (see FIG. 3).

Figure 3A:
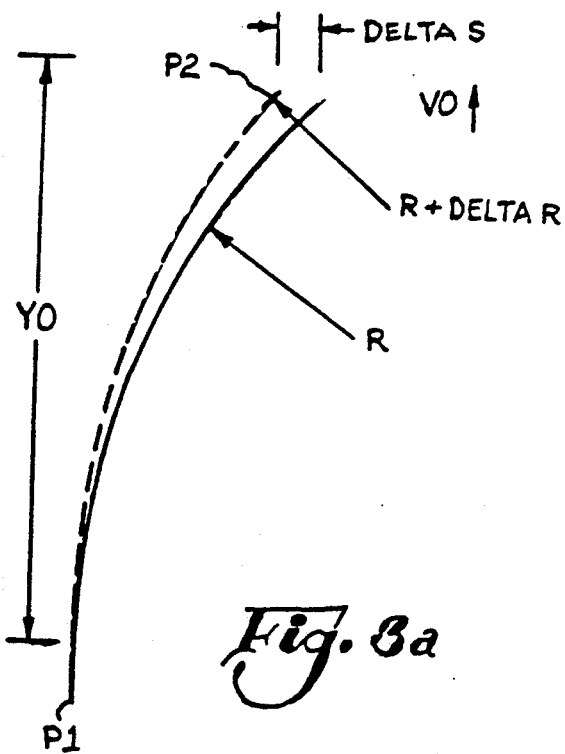
FIG. 3a is a schematic representation of an optical target defining dimensions and parameters used in defining the effect of ablation on radius of curvature of the target surface.

In order to change the radius in the vertical plane by delta r, the removal delta T must correspond to the difference in saggital delta S between the original radius and the new radius at all distances for all points in a vertical plane (see FIG. 3a). Since $$\text{delta } S = \text{delta } R. Y_o^2/2R^2 \qquad (4)$$

where Y is the distance from the center of the lens to a point P in the vertical plane, hence, assuming P1 to be the initial position at the center of the lens $$\text{delta } R = (2K.H.R^2)V_0 \qquad (5)$$

The change in cylinder power is then $$K2.H.N$$

where K2 is a constant independent of the target radius. This allows one to ablate a lens with a radius of curvature in x axis which is different from the radius of curvature in the y axis, hence a toric lens. It should also be noted that the change in cylinder power does not depend upon the initial curvature of the target. For instance a scan that would induce a change in power of 0.25 diopters in a spherical lens will induce the same degree of change in curvature in the optical target surface irregardless of the initial target's radius of curvature.

The ablation profile is, of course, controlled by the product of the beam intensity profile function, which includes a pulse rate function, with the scanning velocity profile function. In the case where the beam pule rate is constant velocity will be related to ablation as $$V = [+]A/Y_o^2$$

where V is the instantaneous velocity of the beam as it is scanned, A is an ablation constant, and $Y_o$ is the distance of the beam from the axis of symmetry of the induced cylinder in the target, where such ablation causes a cylindrical component to be induced into the target surface.

To accomplish combinations of ablation profiles the velocity functions need to be combined so that the resultant profile, Vr, at each point is $$1/Vr = (1/V1 + 1/V2)$$

It is also clear that some degree of ablation must be accounted for at every point in the scan given a fixed pulse rate since the beam cannot be scanned at infinite speed. Thus all ablation profiles will have a constant maximum and minimum ablation component built into them.

The desired ablation profile required to induce a change in cylinder power can also be accomplished by controlling the pulse rate of the laser. Accomplishing a given profile of ablation is dependent upon controlling the product of scan speed as a function of time (V) and the pulse rate of the laser as a function of time.

Alternately, the ablation profile can be controlled with constant sweep velocity by controlling the pulse rate of the laser. It should be obvious that the repetition rate H could be varied instead of or as well as the scan velocity for different points on the surface. The amount of material removed at each point is proportional to the repetition rate as shown in Equation 1. If the velocity is kept uniform, then the variation in repetition rate required to produce any given profile can be readily derived in exactly the same way as for the velocity profile using Equation 1 at each point.

If several types of profile modification are to be accomplished with a uniform velocity, the repetition rate distributions for each individual profile need to be added together at each point and the resulting repetition rate distribution will produce the composite profile.

If the velocity is varied as well as the repetition rate then the ratio of H to V must be used to ensure the etch depth at each point agrees with Equation 1. If multiple profile types are to be added together, then either the repetition rate H or the velocity V must be made the same for each profile distribution for each point. This is a trivial transformation using Equation 1. It should also be obvious that the additive process can still be used where both the repetition rate and velocity change at all points in the distribution because each point can be treated separately. The functions generated for repetition rate and velocity should, however, be continuous over the area to be etched.

The means used to control the movement of the scanning mirror can be provided by a servo-mechanism driven by a stepper motor controlled through digital electronic means. Thus, the velocity profile can be controlled via a computer program and can be of any desired form.

Another way of practicing this invention requires the target optical surface to be moved in a controlled fashion along axis x through the laser beam domain to effect the controlled ablation. This varies from the approach shown in FIG. 2 in that it allows one to move the target rather than the beam.

Apart from the specific apparatus configuration, the fixed target configuration is determined by the initial target configuration and the degree of ablation as a function of x and y across the surface of the target. For instance, it is possible to form a lens from a contact lens button (essentially a disk of contact lens material). In order to form disk into a finished lens, a substantial portion of material must be ablated which will require a substantial time to obtain. On the other hand, the contact lens blank can be substantially in the form of a spherical contact lens. Thus, if one were making a toric lens with relative low toricity, the amount of time required to make the lens would be minimal since only a small amount of ablation along 1 axis would be required to convert the spherical powered lens to a toric lens. Other surfaces which could be altered include corneas, intraocular lenses, spectacles and other optical elements.

One of the significant advantages of the present method vis-a-vis the state of the art methods of forming toric powered contact lenses is that the present method is better able to produce toric lenses with relatively low degrees of toricity (in particular, this is where the radius of curvature along the x axis, R curvature$_x$, is close to the radius of curvature along the y axis, R curvature$_y$. Another advantage of the system is that it is able to produce very accurate high cylinder toric lenses as well. In other words, the two radii being produced in the toric lens can be specified to a degree of precision far greater than is available through state of the art lathing techniques The present method can be used to form both front surface toric lenses and back surface lenses, as one skilled in the art should appreciate. The method can also be used to produce high quality spherical lenses and lenses with bifocal optics and other configurations For instance, bifocal lenses could be produced by masking a domain of the target and inducing spherical power change over the unmasked domain, thus producing a lens with two domains of different powers.

The present method can be used on any plastic contact lens material as long as the radiation source used has sufficient energy and the proper wavelength to induce photo- ablation. Specific materials include the nonhydrated forms of poly 2-hydroxyethylmethacrylate (pHEMA), poly N-vinyl-2-pyrrolidone (pNVP), polymethylmethacrylate(pMMA), and copolymers of the above as well as other contact lens materials known to those skilled in the art. Gas permeable materials may be used as well as silicone based contact lens materials, especially fluorosilicone based materials.

The choice of radiation sources used on any specific type of lens material will be subject to a number of factors; wavelength of radiation, the threshold intensity required to cause photoablation mechanics to predominate over their usual degradation modalities which will depend to some degree upon wavelength and material type), and ambient atmosphere conditions (some ablative modalities are optimized by the presence of reactive gases, others require "inert" atmospheres).

It has also been found that the process of ablating plastic biomedical materials often creates differential stress across the surface of the material which has been ablated. Surprisingly, this affect can be ameliorated by uniformly ablating the whole front surface of the target. By removing this uniform thickness of material, the underlying material is rendered homogeneous at its surface.

The following examples illustrate some of the applications of the present invention. The examples do not exhaust all of the possibilities of the present invention to shape optical target surfaces. No examples are given of corneal shaping although the same procedures used to shape contact lenses could generally be used to shape the optical surface of the eye. In such cases, the cornea would be considered to be a target optical surface.

EXAMPLES

EXAMPLE 1

Figure 4:
FIG. 4 shows the surface of a contact lens with a lathed surface.
Figure 5:
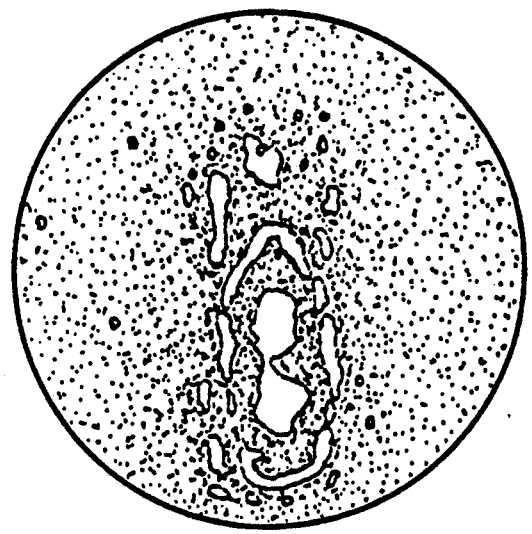
FIGS. 5 and 6 show the interferogram of a toric contact lens made by the claimed process.
Figure 6:
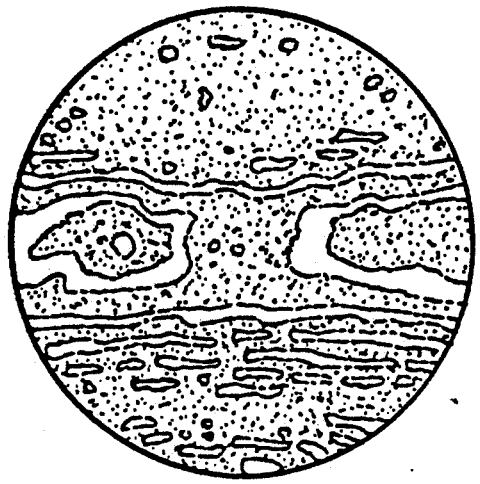

An unhydrated soft contact lens blank with a spherical posterior surface was aligned in the apparatus shown in FIG. 2 as the optical target surface. This lens was made from Polymacon r material, a material widely used to make soft contact lenses. The posterior surface of the lens was scanned by the excimer beam as the scanner was scanned along the z axis in a nonlinear fashion that took more material from the edges of the lens than from the center along one axis. The lens was shown prior to being scanned by the excimer laser to be very close to a perfect sphere by interferometeric means. The interferogram of the lens prior to laser ablation is shown in FIG. 4. The Figure shows that the whole posterior surface of the lens is within a few interference fringes of being spherical which translates to a deviation across the face of the lens of less than 1 micron. After being scanned with the laser, per the method of the invention, the lens is toric. FIGS. 5 and 6 show interferograms along the two axis of the posterior lens surface. As is clearly shown along each of the axis, the lens is within several interference fringes of having a given radii along that axis and some other radii along the other axis. This indicates that the two radii of the toric lens were precisely what had been anticipated. In this case the radii of the two axii were intended to be 6.996 and 7.115 mm and the actual observed radii were 6.991 and 7.108 mm. For comparative purposes, the interferometer of a commercially available toric lens is shown in FIG. 7. Here at least 20 interference fringes can be seen across the posterior surface of the lens.

EXAMPLE 2

A lens blank with a spherical posterior surface was mounted in the apparatus shown in FIG. 2. The lens was then scanned along an axis according to a function which would change the cylinder power of the lens along that axis. The lens was rotated 90 degrees and the lens was scanned again using the same scan function as employed on the first scanning sweep. The lens was then subjected to interferometeric analysis which showed that the spherical power of the lens was changed and that the lens still possessed an almost perfect posterior surface, albeit with a different power than the original blank. The interferogram of the ablated lens is shown in FIG. 8. As can be seen, there are few interference fringes across the whole posterior optical surface of the lens.

The initial radius and final radius of a series of 9 lenses whose spherical radius was altered in this way as shown in Table 1 as well as the corresponding calculated power change in the finished hydrated lens in diopters.

TABLE 1

| | Initial Radius (mm) | Final Radius (mm) | Power Change (mm) |
| --- | --- | --- | --- |
| | 7.496 | 7.581 | 0.58 |
| | 7.493 | 7.569 | 0.52 |
| | 7.499 | 7.586 | 0.64 |
| | 7.500 | 7.587 | 0.59 |
| | 7.493 | 7.569 | 0.52 |
| | 7.502 | 7.586 | 0.57 |
| | 7.502 | 7.586 | 0.57 |
| | 7.493 | 7.583 | 0.61 |
| | 7.497 | 7.589 | 0.63 |
| | 7.501 | 7.593 | 0.63 |
| MEAN | 7.496 | 7.583 | 0.58 ± 0.06 |

EXAMPLE 3

A lens blank with a spherical posterior surface was mounted in the apparatus shown in FIG. 2. The lens was scanned twice along one axis to induce a cylinder then turned through a 90 degree angle and scanned once with the same parameters. These cylindrical components add to produce a sphere change in power and a resultant cylinder change in power. The initial radius of the surface was 7.470 mm. After both sets of scans, the surface had two radii in perpendicular meridians of 7.382 and 7.292, indicating a 0.088 mm change in spherical radius with an additional 0.090 mm cylinder.

What is claimed is:

1. A modified optical surface produced by controllably sweeping the domain of an optical target surface along an axis according to a predetermined sweep velocity profile with a high energy beam in such a fashion as to selectively ablate material in a predetermined fashion along said axis.

2. The optical target surface of claim 1 wherein said sweep velocity profile is defined by the general formula $$V = A//Y_o^2$$

where V is the instantaneous velocity of the beam as it is scanned, A is an ablation constant, and $Y_o$ is the distance of the beam from the axis of symmetry of the induced cylinder in the target, where such ablation causes a cylindrical component to be induced into the target surface.

3. A modified optical surface produced by changing the curvature of radius of said optical target surface by a) controllably sweeping the domain of said optical surface along an axis X according to a predetermined sweep velocity profile with high energy beam in such a fashion as to selectively ablate material in a predetermined fashion along said axis X and b) repeating a) along an axis perpendicular to said axis X used in a).

4. The optical target surface of claim 1 wherein said sweep velocity profile is chosen so as to add prism to said optical surface.

5. The optical target surface of claim 1 wherein said sweep velocity profile is defined so as to remove prism from said optical surface.

6. The optical target surface of claim 1 wherein said optical target surface is modified from an initially spherical surface to a toric surface.

7. The optical target surface of claim 1 wherein said optical surface is an intraocular lens.

8. The optical target surface of claim 1 wherein said optical surface is a cornea.

9. A contact lens modified by controllably sweeping the domain of an optical target surface along an axis according to a predetermined sweep velocity profile with a high energy beam in such a fashion as to selectively ablate material in a predetermined fashion along said axis.

* * * * *